US009536046B2

(12) United States Patent
Gillam et al.

(10) Patent No.: US 9,536,046 B2
(45) Date of Patent: Jan. 3, 2017

(54) AUTOMATED ACQUISITION OF FACIAL IMAGES (75) Inventors: Michael Gillam, Washington, DC (US); John Christopher Gillotte, Washington, DC (US); Craig Frederick Feied, Kirkland, WA (US); Jonathan Alan Handler, Northbrook, IL (US); Renato Reder Cazangi, Rockville, MD (US); Rajesh Kutpadi Hegde, Redmond, WA (US); Zhengyou Zhang, Bellevue, WA (US); Cha Zhang, Sammamish, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1254 days.

(21) Appl. No.: 12/685,686

(22) Filed: Jan. 12, 2010

(65) Prior Publication Data
US 2011/0170739 A1 Jul. 14, 2011

(51) Int. Cl.
G06K 9/00 (2006.01)
G06K 15/02 (2006.01)
G06F 19/00 (2011.01)
G07C 9/00 (2006.01)

(52) U.S. Cl.
CPC ......... G06F 19/322 (2013.01); *G07C 9/00079* (2013.01); *G07C 9/00103* (2013.01)

(58) Field of Classification Search
None
See application file for complete search history.

(56) References Cited

U.S. PATENT DOCUMENTS

| 5,601,314 A * | 2/1997 | Burns et al. ..................... 283/81 |
| 6,297,846 B1 * | 10/2001 | Edanami ....................... 348/239 |
| 6,393,431 B1 | 5/2002 | Salvati et al. |
| 6,621,491 B1 | 9/2003 | Baumrind et al. |
| 7,262,698 B1 * | 8/2007 | Frederick et al. ......... 340/545.6 |
| 7,764,812 B2 * | 7/2010 | McQuaide, Jr. ... G07C 9/00087 340/539.13 |
| 9,218,452 B2 * | 12/2015 | Varna ..................... G06F 19/322 |
| 2001/0026309 A1 * | 10/2001 | Takeyama ..................... 347/224 |

(Continued)

OTHER PUBLICATIONS

Gillam, et al., "Automated Patient Facial Image Capture to Reduce Medical Error", retrieved at <<http://www.pubmedcentral.nih.gov/picrender.fcgi?artid=1839287&blobtype=pdf>>, Mar. 15, 2006, p. 1.

(Continued)

*Primary Examiner* — Chan Park
*Assistant Examiner* — Mia M Thomas
(74) *Attorney, Agent, or Firm* — Michael David Ream; Tom Wong; Micky Minhas (57) ABSTRACT Described is a technology by which medical patient facial images are acquired and maintained for associating with a patient's records and/or other items. A video camera may provide video frames, such as captured when a patient is being admitted to a hospital. Face detection may be employed to clip the facial part from the frame. Multiple images of a patient's face may be displayed on a user interface to allow selection of a representative image. Also described is obtaining the patient images by processing electronic documents (e.g., patient records) to look for a face pictured therein.

20 Claims, 6 Drawing Sheets (56) References Cited

U.S. PATENT DOCUMENTS

| | | | |
|---|---|---|---|
| 2002/0067925 A1* | 6/2002 | Yamano | B41J 2/205 399/1 |
| 2002/0115912 A1* | 8/2002 | Muraki et al. | 600/300 |
| 2002/0179094 A1* | 12/2002 | Perlow | 128/897 |
| 2004/0003295 A1* | 1/2004 | Elderfield et al. | 713/202 |
| 2004/0208343 A1* | 10/2004 | Golden et al. | 382/110 |
| 2005/0027197 A1* | 2/2005 | Segawa | A61B 6/00 600/463 |
| 2005/0065411 A1* | 3/2005 | Baldwin et al. | 600/240 |
| 2005/0075907 A1* | 4/2005 | Rao | 705/2 |
| 2006/0036469 A1* | 2/2006 | Munday | 705/2 |
| 2006/0149600 A1* | 7/2006 | Cavanaugh et al. | 705/3 |
| 2006/0184027 A1* | 8/2006 | Watanabe et al. | 600/440 |
| 2006/0193502 A1* | 8/2006 | Yamaguchi | 382/118 |
| 2006/0253346 A1* | 11/2006 | Gomez | 705/28 |
| 2007/0122005 A1* | 5/2007 | Kage et al. | 382/115 |
| 2007/0124973 A1* | 6/2007 | Stallings | G09F 3/005 40/633 |
| 2007/0172155 A1* | 7/2007 | Guckenberger | 382/305 |
| 2007/0186923 A1* | 8/2007 | Poutiatine et al. | 128/200.14 |
| 2007/0192138 A1* | 8/2007 | Saito et al. | 705/3 |
| 2007/0232885 A1* | 10/2007 | Cook et al. | 600/407 |
| 2007/0288268 A1 | 12/2007 | Weeks | |
| 2007/0299776 A1* | 12/2007 | Frustaci et al. | 705/50 |
| 2008/0056580 A1* | 3/2008 | Okada | H04N 5/23219 382/190 |
| 2008/0267447 A1* | 10/2008 | Kelusky et al. | 382/100 |
| 2008/0279427 A1* | 11/2008 | Takagi | 382/118 |
| 2008/0292151 A1 | 11/2008 | Kurtz et al. | |
| 2008/0301982 A1* | 12/2008 | Kaufman | 40/310 |
| 2009/0024416 A1 | 1/2009 | McLaughlin et al. | |
| 2009/0037222 A1* | 2/2009 | Kuo | 705/3 |
| 2009/0116703 A1* | 5/2009 | Schultz | 382/118 |
| 2009/0124863 A1 | 5/2009 | Liu et al. | |
| 2009/0125329 A1* | 5/2009 | Kuo | 705/3 |
| 2009/0187424 A1* | 7/2009 | Grabowski | 705/3 |
| 2009/0204436 A1* | 8/2009 | Thorne et al. | 705/3 |
| 2009/0316168 A1* | 12/2009 | Enjuji | G06K 9/00234 358/1.9 |
| 2010/0014721 A1* | 1/2010 | Steinberg et al. | 382/118 |
| 2010/0067750 A1* | 3/2010 | Matsuo | G06F 17/30265 382/118 |
| 2010/0094653 A1* | 4/2010 | Tribble et al. | 705/3 |
| 2010/0166316 A1* | 7/2010 | Choi | H04N 1/00336 382/190 |
| 2010/0191071 A1* | 7/2010 | Anderson et al. | 600/301 |
| 2010/0217623 A1* | 8/2010 | Schoenberg et al. | 705/3 |
| 2010/0241444 A1* | 9/2010 | Young | 705/2 |
| 2011/0096963 A1* | 4/2011 | Shekhara | G06F 19/321 382/128 |
| 2011/0234831 A1* | 9/2011 | Ando | H04N 7/14 348/222.1 |
| 2011/0280466 A1* | 11/2011 | Cho et al. | 382/133 |
| 2012/0002878 A1* | 1/2012 | Kuriyama | 382/195 |
| 2012/0114268 A1* | 5/2012 | Kajihara et al. | 382/305 |
| 2013/0141605 A1* | 6/2013 | Kim | G06T 11/60 348/222.1 |
| 2013/0195329 A1* | 8/2013 | Canda | G06F 19/321 382/128 |
| 2014/0013710 A1* | 1/2014 | Behman | 53/411 |
| 2014/0059980 A1* | 3/2014 | Moncrief et al. | 53/467 |
| 2014/0275948 A1* | 9/2014 | Kamisoyama | A61B 5/6898 600/407 |
| 2015/0157243 A1* | 6/2015 | Do | A61B 5/1032 600/408 |
| 2015/0261996 A1* | 9/2015 | Kim | G06K 9/00255 348/14.03 |
| 2016/0006941 A1* | 1/2016 | Kim | G06K 9/00255 348/77 |

OTHER PUBLICATIONS

Zhang, et al., Image-Based Electronic Patient Records for Secured Collaborative Medical Applications, retrieved at <<http://ieeexplore.ieee.org/stamp/stamp.jsp?tp=&arnumber=1617161>>, proceedings of the 2005 IEEE Engineering in Medicine and Biology 27th Annual Conference Shanghai, China, Sep. 1-4, 2005, pp. 3.

S.L.B Dove, "The Management of Digital Clinical Images & Video Recordings", retrieved at<<http://www.nnuh.nhs.uk/viewdoc.asp?ID=108&t=TrustDoc>>, Oct. 2004, pp. 1-11.

"Florida Agency for Health Care Administration Point of Care Model Electronic Health Record Demonstration Project Application", retrieved at<<http://www.fhin.com/FHIN/workgroups/MeetingMaterials/Dec0208/GladesGeneralHospitalApplAndAppend.pdf>>, Oct. 29, 2008, pp. 69.

* cited by examiner

| PICTURE | MRN | INSTITUTION | ADMITDATETIME | FNAME | MNAME | LNAME | ADMITTINGNAME | DISCHARGEDATETIME | LOCUNIT |
|---|---|---|---|---|---|---|---|---|---|
| IMAGE P1 | 841233 | WHC | 04/07/2008 07:30 | --- | X | --- | --- | 04/07/2008 10:30 | |
| IMAGE P2 | 842564 | WHC | 04/07/2008 09:31 | --- | Y | --- | --- | 04/07/2008 13:30 | |
| IMAGE P3 | 845757 | WHC | 04/07/2008 15:18 | --- | Z | --- | --- | 04/07/2008 14:30 | |
| IMAGE P4 | 845998 | WHC | 04/07/2008 18:30 | --- | | --- | --- | 04/07/2008 10:30 | |
| IMAGE | 847733 | FSH | 04/07/2008 22:00 | --- | A | --- | --- | 04/07/2008 03:00 | MRI |
| IMAGE P5 | 848452 | GUH | 04/08/2008 01:22 | --- | B | --- | --- | 04/09/2008 02:30 | |

AUTOMATED ACQUISITION OF FACIAL IMAGES

BACKGROUND

In the field of medicine, patient misidentification is a significant problem that often results in harm to patients, particularly in hospital environments where there are various procedures and treatments that patients undergo, and many different areas within each hospital. For example, misidentification can lead to one patient being harmed by missing out on needed treatment, while another patient unnecessarily gets the treatment instead, which may be potentially harmful to that patient.

One estimate is that as high as thirty percent of errors in medicine are due to patient identity errors. Any technology that reduces such errors is highly desirable.

SUMMARY

This Summary is provided to introduce a selection of representative concepts in a simplified form that are further described below in the Detailed Description. This Summary is not intended to identify key features or essential features of the claimed subject matter, nor is it intended to be used in any way that would limit the scope of the claimed subject matter.

Briefly, various aspects of the subject matter described herein are directed towards a technology by which patient facial images are acquired and maintained with those patients' respective medical-related data. An acquisition mechanism receives images of patients, and obtains information (e.g., via a face detection algorithm) as to where the patient's face appears within the image. This region is clipped and maintained as a patient facial image in association with patient data, e.g., at least data by which the patient may be further identified.

In one aspect, multiple patient images are obtained by sampling frames provided by a video camera or by collecting snapshots. The patient images are presented on an interactive user interface that allows selection of one of the images for associating with that patient.

In an alternative implementation, patient images are obtained by processing electronic documents (e.g., patient records) to look for a face pictured therein. Each face that is found may be maintained in association with other data for that patient.

Other advantages may become apparent from the following detailed description when taken in conjunction with the drawings.

BRIEF DESCRIPTION OF THE DRAWINGS

The present invention is illustrated by way of example and not limited in the accompanying figures in which like reference numerals indicate similar elements and in which.

DETAILED DESCRIPTION

Various aspects of the technology described herein are generally directed towards automatically acquiring facial images and using those images for patient identification in medical environments, such as hospitals and clinics. In one aspect, the facial images may be captured by a camera, such as during a live video capture of a patient triage or other admission process. In another aspect, the facial images may be captured from documents containing pictures of patients, such as patient records that include photographic copies of driver's license photographs. Once the images are acquired, they may be used in numerous ways to help correctly identify a patient, including in user interfaces as exemplified herein, on printed records and/or charts, on printed medicine bottle labels, and so forth.

While Microsoft Amalga® UIS, a unified intelligence system/service that provides client users with access to clinical data, is used as an example herein of a system in which the acquired patient images may be used, it should be understood that any of the examples described herein are non-limiting examples. As such, the present invention is not limited to any particular embodiments, aspects, concepts, structures, functionalities or examples described herein. Rather, any of the embodiments, aspects, concepts, structures, functionalities or examples described herein are non-limiting, and the present invention may be used various ways that provide benefits and advantages in computing, displaying facial images, and user interface elements in general.

Figure 1:
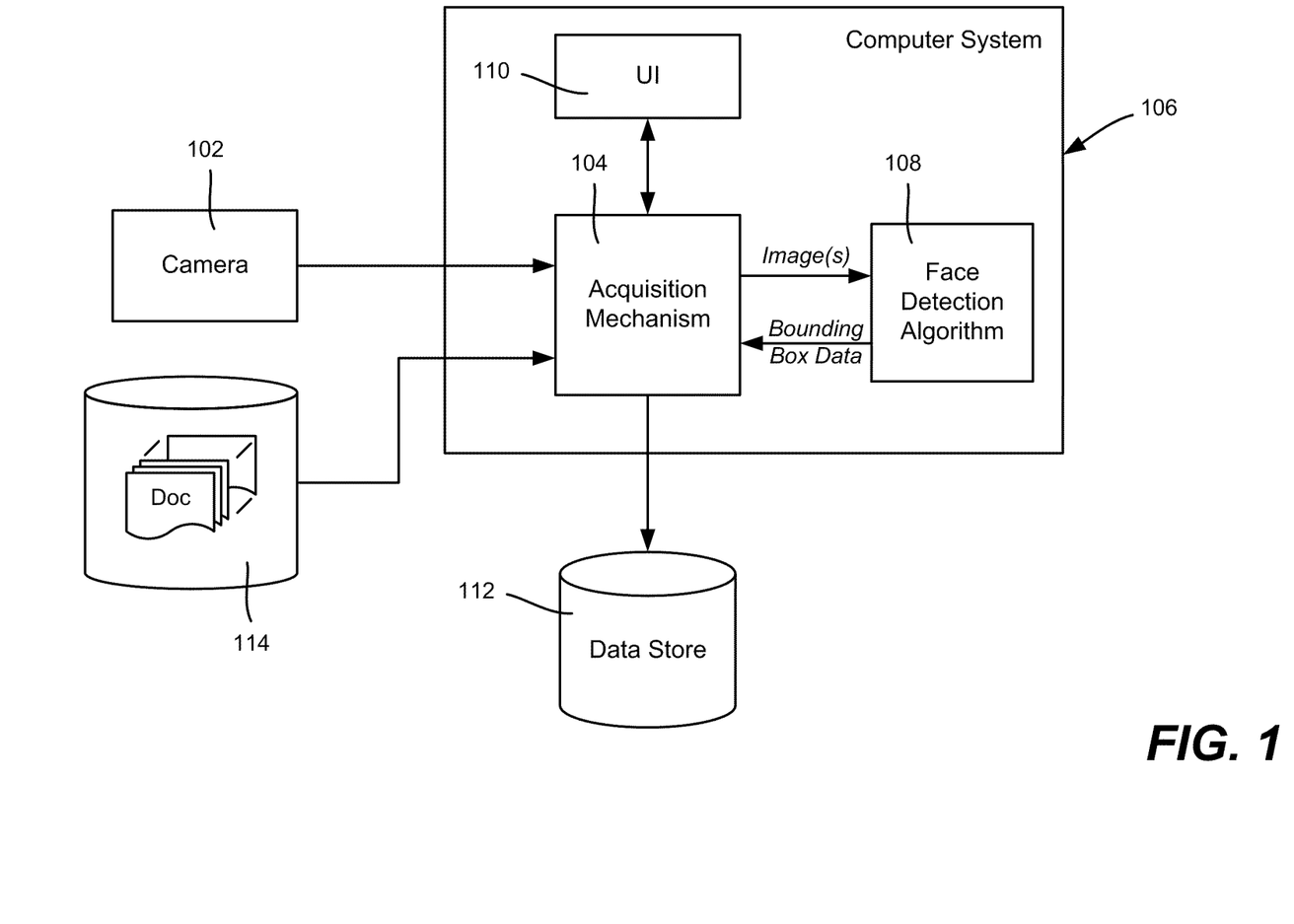
FIG. 1 is a block diagram showing example components for acquiring and maintaining patient facial images.

FIG. 1 shows various aspects related to an automated or semi-automated acquisition process. In one implementation, a camera 102 provides a live video feed to an acquisition mechanism 104 running on a computer system 106. The acquisition mechanism 104 sends one or more images (each a video frame) to a face detection algorithm 108, which returns bounding box data for each image indicative of where the patient's face appears within the frame. Note that many known face detection algorithms are suitable for this purpose, and such face detection algorithms are not described in detail herein.

Figure 2:
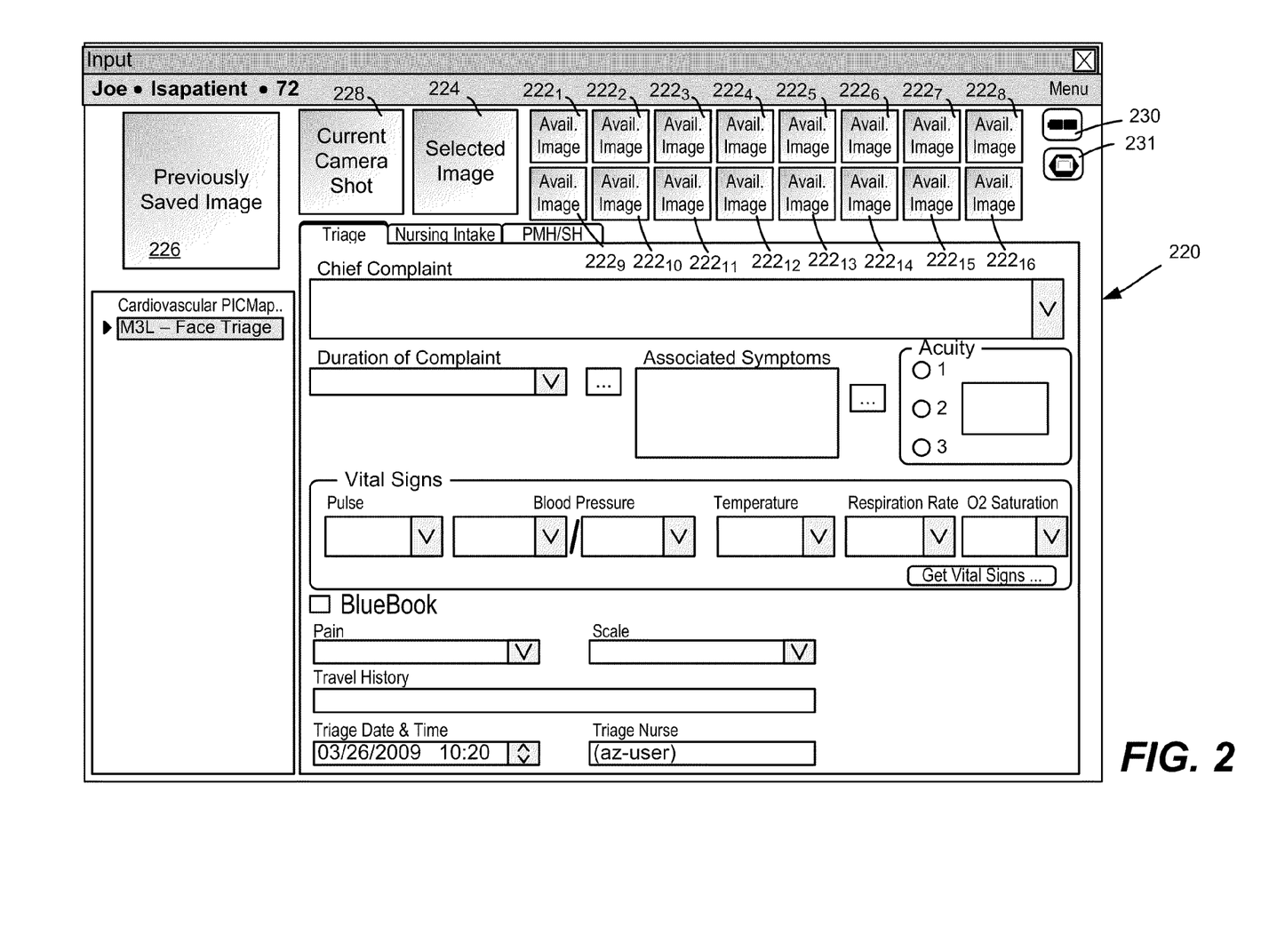
FIG. 2 is a screenshot representation of an example user interface display for viewing and interacting to select a patient facial image.

With the bounding box data, the acquisition mechanism 104 clips the face portion from the image for output to a user interface 110, such as the triage-related user interface display 220 further represented in FIG. 2. This process may be repeated some number of times (over some number of frames) to obtain a plurality of different available images $222_1$-$222_{16}$. From the user interface, an operator (e.g., a triage nurse) may select an image as a representative currently selected image 224 for that patient, while inputting other information regarding that patient.

In the example of FIG. 2, sixteen available images $222_1$-$222_{16}$ are shown to the operator, but as can be readily appreciated any practical number may be presented, (even only one that the operator can either accept or retake). In this example, the operator selects one from the available ones, such as by clicking on one (or one may be saved by default if no selection is made). This is shown as the currently selected image 224, e.g., slightly larger than the available image that was clicked. Also shown is a previously saved image 226, if any, for the patient, such as from a previous visit, and a shot 228 of what the camera is currently viewing.

In general, the purpose of having multiple images available for selection is to find one that represents the patient well. For example, as the patient moves his or her face, the viewing angle, lighting and so forth will change, whereby some images will be more appropriate than others. Similarly, the patient may be speaking, rubbing his or her eyes and so forth, whereby some images may be less suitable for use. Thus, the frames are typically sampled over a relatively longer time (rather than acquired at the camera frame rate), e.g., once every few seconds. Note that instead of a video camera, a still camera may be used to snap the set of images, e.g., at a desired rate. Further, controls 230, 231 may be provided to allow the operator to obtain one or more retakes.

In this manner, at least one image is associated with the patient's records from the very first admission. To this end, as part of the triaging process, the selected image 224 is saved in conjunction with other data for that patient (at least in association with a patient identifier) to a data store 112 (FIG. 1), or a set of data stores as appropriate. Note that more than one image may be saved, e.g., an image from a previous visit and a current image may both be retained, differentiated by timestamps or the like. Thus, the system may populate images from previous visits automatically.

Note that it is also feasible to use prerecorded video or snapshots rather than live video/snapshots as the source of the image or images. However, anything captured at an earlier time needs to be matched up with the other patient data in some way, possibly by timestamps, operator/camera ID and so forth. Also, extra care may be taken to ensure that the matching is correct, e.g., a human operator selecting the representative image may also listen to the audio where the person speaks/spells his or her name and match the spoken name to the associated text records.

FIG. 1 further shows another alternative, in which the image is obtained from saved data, such as documents in a patient records data store 114. In many hospitals, it has been the practice to obtain a copy of a patient's driver's license whenever possible. The copy including the photograph on the driver's license then becomes part of the patient's file/records. Any other facial image that is available in a patient's records may be used in a similar manner.

In many environments, such patient records have been scanned or are in the process of being scanned into electronic documents for safer and cheaper storage. During the scanning process, or by automatically reprocessing previously-scanned electronic files, the acquisition mechanism 104 in conjunction with the face detection algorithm 108 may obtain an image from the electronic documents. These may be stored in the data store 112 (or in a different data store), such as in a relational database or the like to provide efficient access, in contrast to being randomly located among the various documents in the records.

Figure 3:
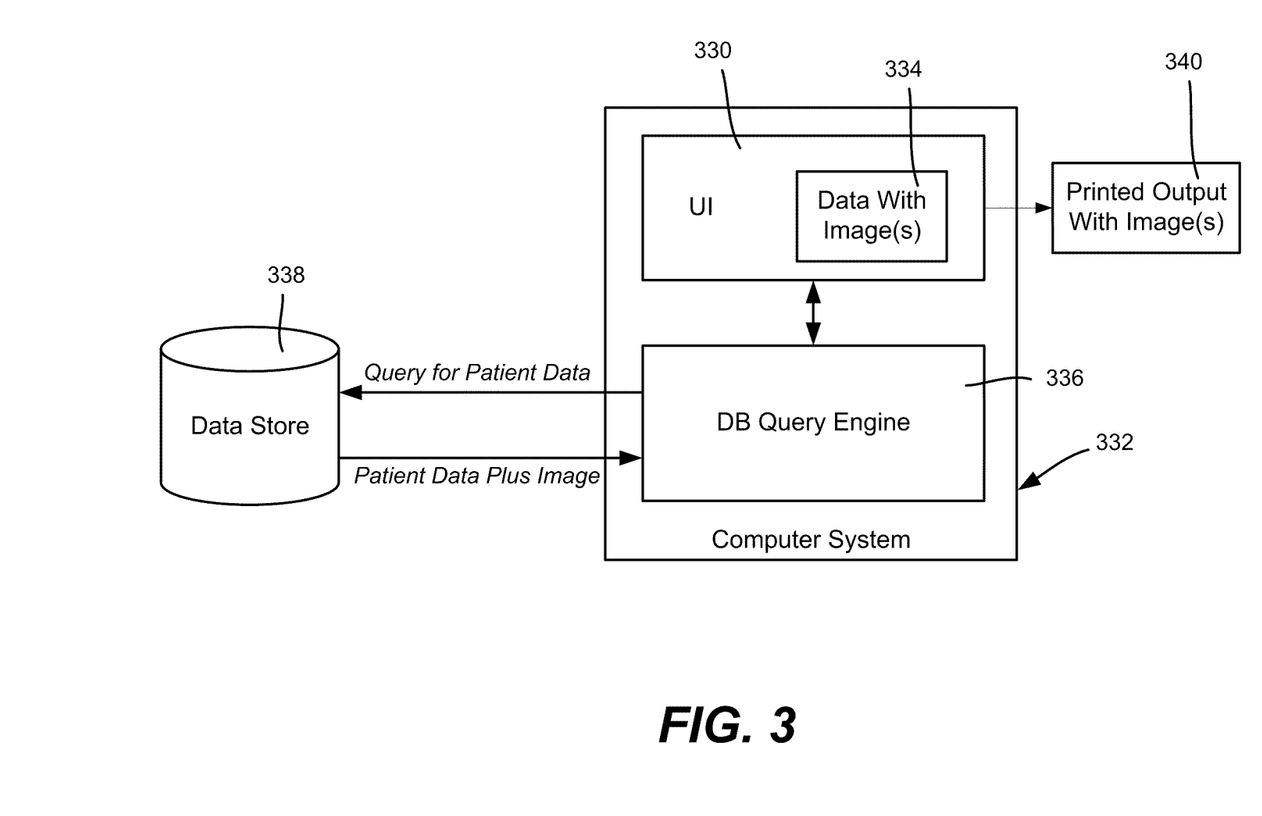
FIG. 3 is a block diagram showing example components for using maintained patient facial images for association with patient data.
Figure 4:
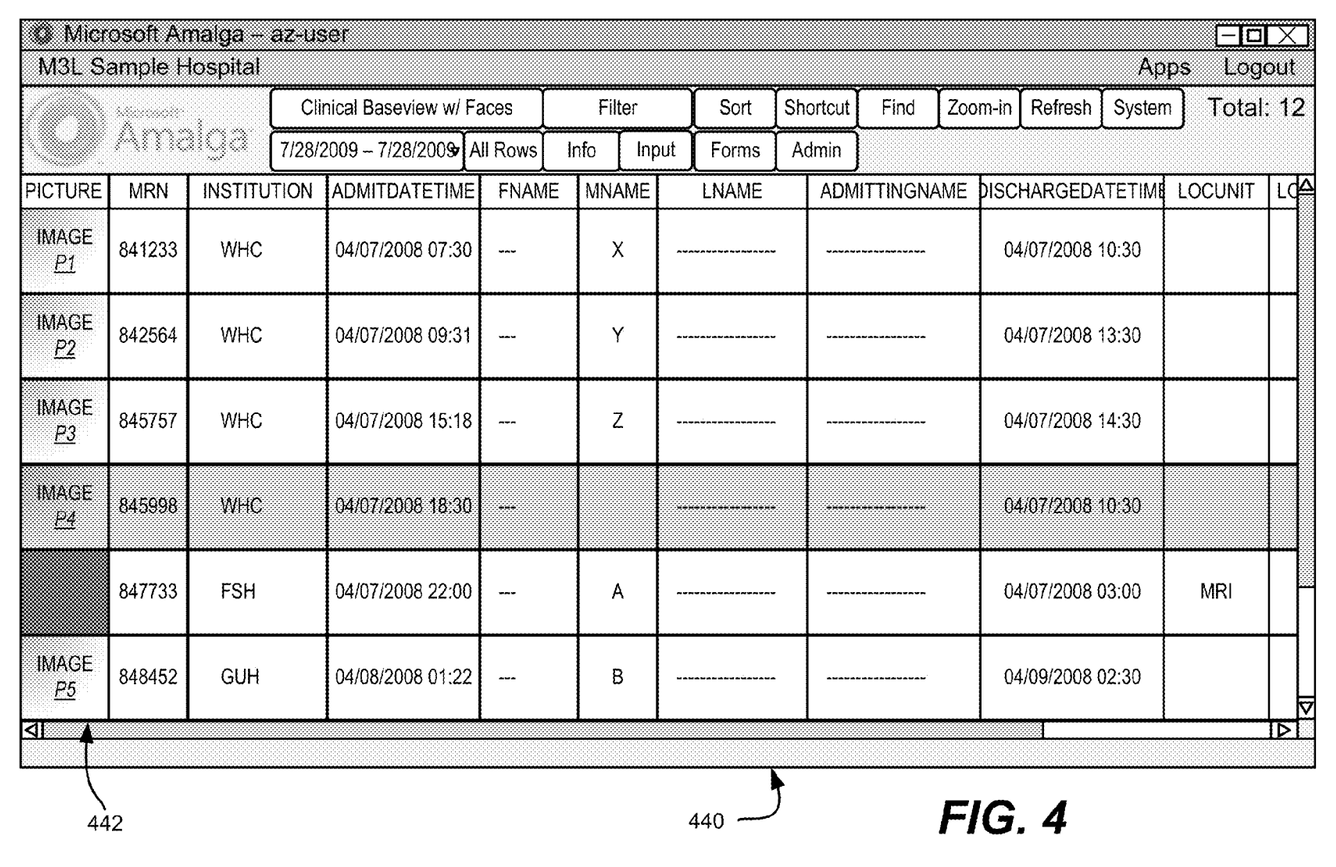
FIG. 4 is a screenshot representation of an example user interface display for viewing facial images and their respective medical data.

Thus, once the image is associated with a patient's identity and possibly other records, the image may be quickly retrieved and used with any other data retrieved for that patient. FIGS. 3 and 4 show an example of how this may be accomplished.

In the example of FIGS. 3 and 4, a user interface 330 of a computer system 332 is populated with the data for various patients, including their images (block 334), such as represented in the example multiple-patient interactive display 440 of FIG. 4. To this end, depending on what the user interface is configured to show, a database query engine 336 or the like queries a data store (or multiple data stores) 338, which may be the data store 112 of FIG. 1) and obtains the desired patient data, including any image for each patient. The user interface 330 then displays the patient data along with the image for each patient.

As also shown in FIG. 3 is the output of a printed image 340 (e.g., printed by a suitable user interface or other program) onto a physical item. The image may go onto a printed chart or record as one type of item, for example, but also may be printed for other patient-associated items. For example, a patient image may be printed on a label of a drug bottle, an IV bag, a food tray carrying a specially prepared meal, and so on to help ensure correct delivery.

In the example screenshot of FIG. 4, the patient images P1-P5 appear in a picture column 442 of a grid, in which each row represents a patient (one row corresponding to the patient with image P4 is highlighted for interaction). The other columns provide additional patient data. In this manner, the patient image accompanies the data about that patient. Note that if desired, any of the columns including the picture column 442 can be fixed from left-to-right scrolling, so that scrolling left-to-right to view further columns does not cause the images to be scrolled off of the screen.

Note that as represented by the blank area between the patient images P4 and P5 in column 442, it is possible that in a given row, the patient image is missing, such as if the patient's last visit was before the use of a camera during triage/admission, and that patient's records have not been scanned/processed to find an image; (as described above, one or more images from previous visits may be used to populate any user interface as needed, but there may not have been any previous visit). Also, the face detection algorithm may have erred and provided bounding box data that was not of a face. In such an event, that patient's identity may be noted in some way (e.g., flagged or added to a list) as needing an image. Then, only that patient's documents need be processed, along with the documents for any other patients having missing images, by the offline acquisition mechanism. In other words, rather than process electronic documents for all patients to obtain facial images, only those where there is no already existing camera-captured image need to be processed. However, there may not be any image in the records, and this can likewise be noted so as to not have the offline acquisition mechanism keep reattempting to find one.

Figure 5:
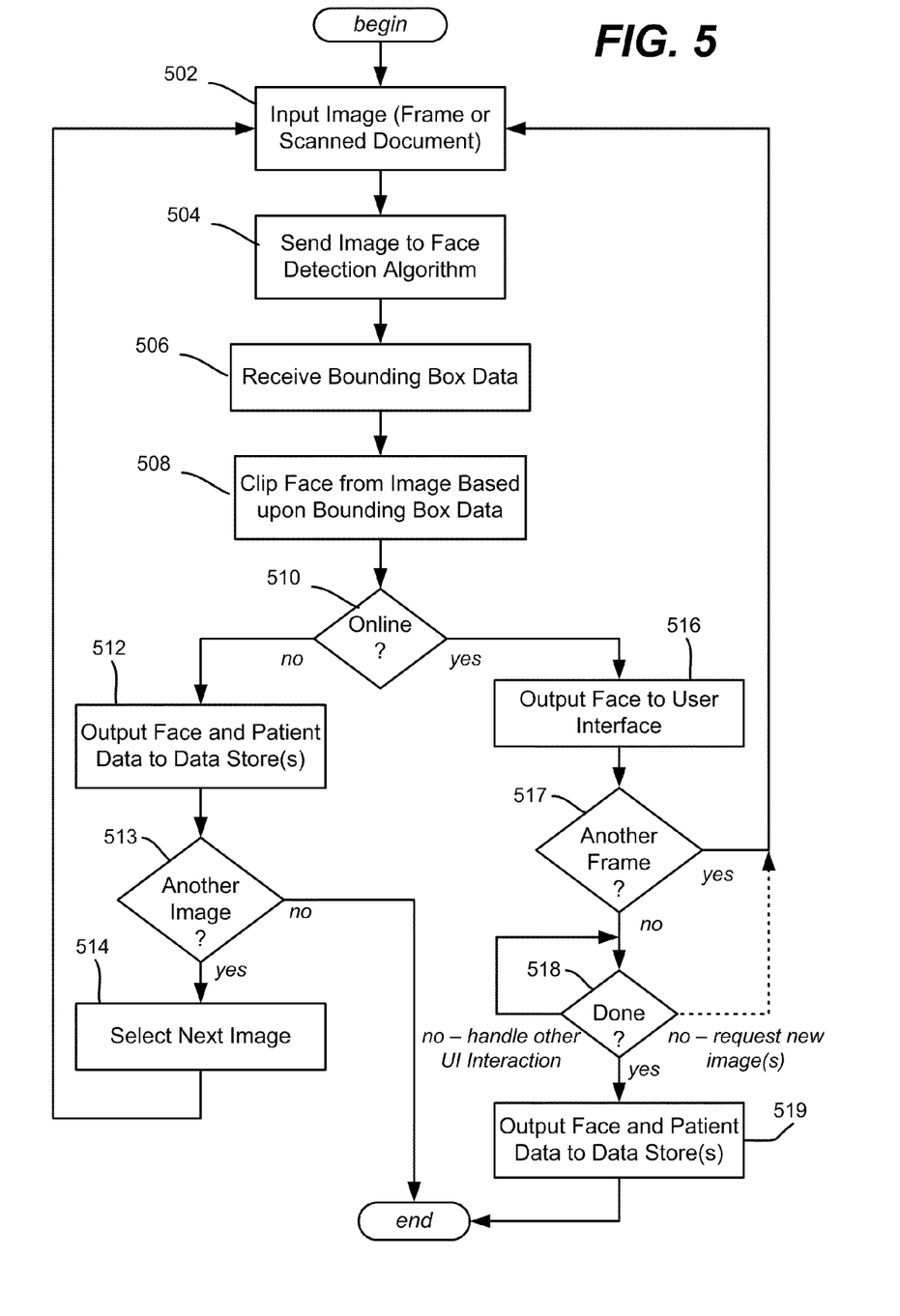
FIG. 5 is a flow diagram showing example steps that may be taken to acquire and maintain patient facial images of multiple patients in association with their respective medical data.

FIG. 5 is a flow diagram summarizing example steps that may be taken by the acquisition mechanism 104, beginning at step 502 when an image (e.g., a video frame or a scanned document) is input into the system. As described above, at step 504 the image is sent to a face detection algorithm, which returns bounding box data (e.g., coordinates or the like) that identify the face's location, as represented by step 506. With the bounding box data, the face within the image may be clipped (step 508) so as to eliminate the unneeded portion of the image.

Step 510 represents the different operating modes of the acquisition mechanism, namely whether the acquisition mechanism is working with online (e.g., live) video and an operator, or is automatically processing scanned documents. Note that this is only an example, as one such acquisition mechanism may operate in different modes, but alternatively may be separate programs, e.g., an online acquisition mechanism that assists an operator may be different code from the offline acquisition mechanism that processes scanned documents.

Steps 512-514 represent the offline document scanning mode (or separate program), which at step 512 outputs the face in association with other patient data to a data store. Note that text recognition also may be employed, e.g., the text on a driver's license may be recognized to correlate with the other patient information.

Steps 513 and 514 represent repeating the acquisition process until the scanned records/documents have been processed as desired, e.g., all of them that are available. Note that this allows for automated acquisition of the faces, with little or no need for human intervention, except for starting the acquisition mechanism, e.g., running the program and pointing it to the set of electronic files to be processed.

Steps 516-519 represent the online video processing mode (or separate program), which at step 516 outputs the face to a user interface as an image that is available for selection. Step 517 repeats the process for other frames, such as to obtain the sixteen available candidate images in the example of FIG. 2. As mentioned above, the frames that are used may be obtained via periodic, random, occasional or other sampling of those being captured so as to obtain a variety of images over a reasonable time.

Once the available frames are shown to the operator, the acquisition mechanism waits for further instruction from the user interface, as represented by step 518. Typically the operator performs whatever user interface interaction is desired, e.g., types in patient data, selects a representative image, and so forth, and then completes the user interface interaction for this patient. However, as represented in FIG. 5 by the dashed line from step 518, it is possible that the operator may request a retake of the images (or a single image), in which event the acquisition mechanism returns to step 502 to restart the online acquisition process. When done, step 519 outputs the selected face (selected by the operator, or if not, by default) in association with the other patient data to the one or more data stores.

Other benefits may be provided by having the patient images associated with patient names and other data. As one example, many patients have common names, and the facial image may be used to differentiate among those patients. As another example, when dealing with an unknown patient who is unable to give his or her name, facial recognition may be used to match the patient's current facial image to previous images and thereby obtain a narrowed list of possible names.

Another problem occurs when joining databases from different hospitals into a master patient index. The same person may be in both databases, possibly with different addresses because of moving between hospital visits. The facial images may be used to help in determining whether two or more patient entries are actually regarding the same person.

Exemplary Operating Environment

Figure 6:
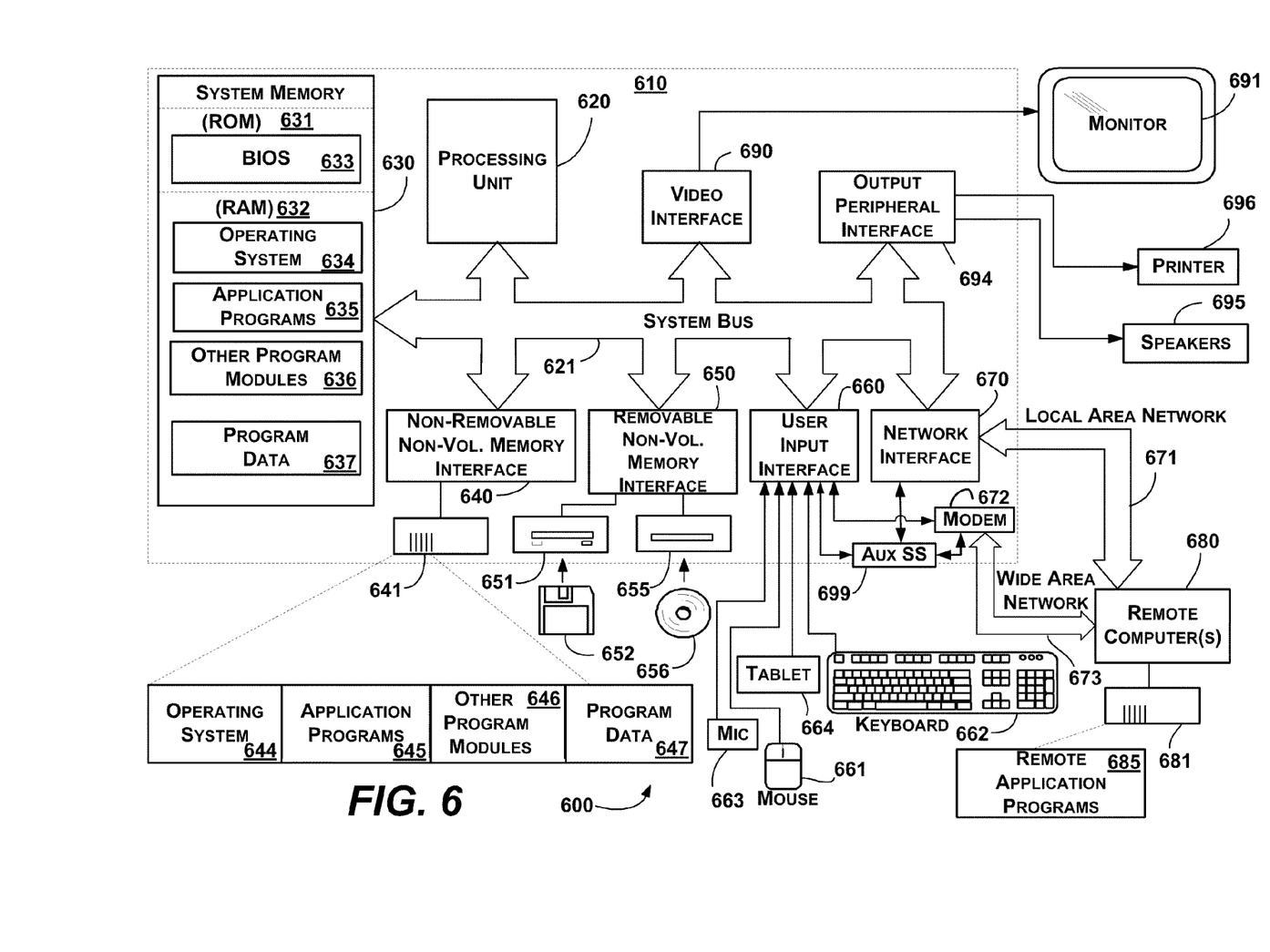
FIG. 6 shows an illustrative example of a computing environment into which various aspects of the present invention may be incorporated.

FIG. 6 illustrates an example of a suitable computing and networking environment 600 on which the examples of FIGS. 1-5 may be implemented. The computing system environment 600 is only one example of a suitable computing environment and is not intended to suggest any limitation as to the scope of use or functionality of the invention. Neither should the computing environment 600 be interpreted as having any dependency or requirement relating to any one or combination of components illustrated in the exemplary operating environment 600.

The invention is operational with numerous other general purpose or special purpose computing system environments or configurations. Examples of well known computing systems, environments, and/or configurations that may be suitable for use with the invention include, but are not limited to: personal computers, server computers, hand-held or laptop devices, tablet devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in local and/or remote computer storage media including memory storage devices.

With reference to FIG. 6, an exemplary system for implementing various aspects of the invention may include a general purpose computing device in the form of a computer 610. Components of the computer 610 may include, but are not limited to, a processing unit 620, a system memory 630, and a system bus 621 that couples various system components including the system memory to the processing unit 620. The system bus 621 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 610 typically includes a variety of computer-readable media. Computer-readable media can be any available media that can be accessed by the computer 610 and includes both volatile and nonvolatile media, and removable and non-removable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by the computer 610. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above may also be included within the scope of computer-readable media.

The system memory 630 includes computer storage media in the form of volatile and/or nonvolatile memory such as read only memory (ROM) 631 and random access memory (RAM) 632. A basic input/output system 633 (BIOS), containing the basic routines that help to transfer information between elements within computer 610, such as during start-up, is typically stored in ROM 631. RAM 632 typically contains data and/or program modules that are immediately accessible to and/or presently being operated on by processing unit 620. By way of example, and not limitation, FIG. 6 illustrates operating system 634, application programs 635, other program modules 636 and program data 637.

The computer 610 may also include other removable/non-removable, volatile/nonvolatile computer storage media. By way of example only, FIG. 6 illustrates a hard disk drive 641 that reads from or writes to non-removable, nonvolatile magnetic media, a magnetic disk drive 651 that reads from or writes to a removable, nonvolatile magnetic disk 652, and an optical disk drive 655 that reads from or writes to a removable, nonvolatile optical disk 656 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 641 is typically connected to the system bus 621 through a non-removable memory interface such as interface 640, and magnetic disk drive 651 and optical disk drive 655 are typically connected to the system bus 621 by a removable memory interface, such as interface 650.

The drives and their associated computer storage media, described above and illustrated in FIG. 6, provide storage of computer-readable instructions, data structures, program modules and other data for the computer 610. In FIG. 6, for example, hard disk drive 641 is illustrated as storing operating system 644, application programs 645, other program modules 646 and program data 647. Note that these components can either be the same as or different from operating system 634, application programs 635, other program modules 636, and program data 637. Operating system 644, application programs 645, other program modules 646, and program data 647 are given different numbers herein to illustrate that, at a minimum, they are different copies. A user may enter commands and information into the computer 610 through input devices such as a tablet, or electronic digitizer, 664, a microphone 663, a keyboard 662 and pointing device 661, commonly referred to as mouse, trackball or touch pad. Other input devices not shown in FIG. 6 may include a joystick, game pad, satellite dish, scanner, or the like. These and other input devices are often connected to the processing unit 620 through a user input interface 660 that is coupled to the system bus, but may be connected by other interface and bus structures, such as a parallel port, game port or a universal serial bus (USB). A monitor 691 or other type of display device is also connected to the system bus 621 via an interface, such as a video interface 690. The monitor 691 may also be integrated with a touch-screen panel or the like. Note that the monitor and/or touch screen panel can be physically coupled to a housing in which the computing device 610 is incorporated, such as in a tablet-type personal computer. In addition, computers such as the computing device 610 may also include other peripheral output devices such as speakers 695 and printer 696, which may be connected through an output peripheral interface 694 or the like.

The computer 610 may operate in a networked environment using logical connections to one or more remote computers, such as a remote computer 680. The remote computer 680 may be a personal computer, a server, a router, a network PC, a peer device or other common network node, and typically includes many or all of the elements described above relative to the computer 610, although only a memory storage device 681 has been illustrated in FIG. 6. The logical connections depicted in FIG. 6 include one or more local area networks (LAN) 671 and one or more wide area networks (WAN) 673, but may also include other networks. Such networking environments are commonplace in offices, enterprise-wide computer networks, intranets and the Internet.

When used in a LAN networking environment, the computer 610 is connected to the LAN 671 through a network interface or adapter 670. When used in a WAN networking environment, the computer 610 typically includes a modem 672 or other means for establishing communications over the WAN 673, such as the Internet. The modem 672, which may be internal or external, may be connected to the system bus 621 via the user input interface 660 or other appropriate mechanism. A wireless networking component such as comprising an interface and antenna may be coupled through a suitable device such as an access point or peer computer to a WAN or LAN. In a networked environment, program modules depicted relative to the computer 610, or portions thereof, may be stored in the remote memory storage device. By way of example, and not limitation, FIG. 6 illustrates remote application programs 685 as residing on memory device 681. It may be appreciated that the network connections shown are exemplary and other means of establishing a communications link between the computers may be used.

An auxiliary subsystem 699 (e.g., for auxiliary display of content) may be connected via the user interface 660 to allow data such as program content, system status and event notifications to be provided to the user, even if the main portions of the computer system are in a low power state. The auxiliary subsystem 699 may be connected to the modem 672 and/or network interface 670 to allow communication between these systems while the main processing unit 620 is in a low power state.

CONCLUSION

While the invention is susceptible to various modifications and alternative constructions, certain illustrated embodiments thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

What is claimed is:

1. In a computing environment, a computer-implemented method performed on at least one processor, the method comprising:
    determining that data associated with a patient does not have an image representative of the patient assigned to the data;
    based on determining that data associated with a patient does not have an image of the patient assigned to the data, automatically acquiring a patient image from documents associated with the patient;
    obtaining information for the image that indicates a bounded region indicative of where the patient's face appears within a frame of the patient image;
    clipping the bounded region from the patient image to obtain a patient facial image;
    maintaining the patient facial image in association with the data associated with the patient; and printing patient facial image data corresponding to the image to a medical item associated with the patient.

2. The computer-implemented method of claim 1 further comprising:
automatically acquiring an additional image of the patient by sampling frames of images of the patient provided by a camera;
obtaining information for the additional image that indicates a bounded region indicative of where-the patient's face appears within a frame of the additional image;
clipping the bounded region from the additional image to obtain an additional patient facial image;
assigning the additional patient facial image to a current patient visit; and
maintaining the additional patient facial image in association with the data associated with the patient.

3. The computer-implemented method of claim 1 further comprising:
receiving at least one other image of the patient;
obtaining information for the other image that indicates a bounded region indicative of where the patient's face appears within the other image;
clipping the bounded region from the image to obtain another patient facial image; and
presenting both the patient facial image and the other patient facial image for selection via a user interface.

4. The computer-implemented method of claim 1 further comprising automatically processing electronic documents for images of the patient.

5. The computer-implemented method of claim 1 further comprising outputting the patient facial image to a user interface that shows data of the patient in association with the patient facial image.

6. The computer-implemented method of claim 5 further comprising outputting one or more of the following: a previously saved patient facial image on the user interface, and a current camera shot on the user interface.

7. The computer-implemented method of claim 1 further comprising outputting the patient facial image to a user interface along with a patient facial image of a different patient, patient facial images being accompanied by data by which the patients are able to be differentiated from one another.

8. In a computing environment, a system comprising:
an acquisition mechanism coupled to a source of patient images, the acquisition mechanism further coupled to a face detection algorithm that automatically locates a facial image of a patient within an image of a document based on a determination that data associated with the patient does not have a patient facial image representative of the patient assigned to the data, the acquisition mechanism configured to automatically acquire a patient image from documents associated with the patient and clip the patient facial image from the patient image based upon data received from the face detection algorithm, and maintain patient facial image in a data store in association with information about the patient; and
a printing device configured to print facial image data corresponding to the patient facial image to a medical item associated with the patient.

9. The system of claim 8 wherein the source of patient images comprises a data store of electronic documents.

10. The system of claim 8 wherein the source of patient images comprises a camera.

11. The system of claim 10 further comprising a user interface that displays a plurality of available facial images for the patient captured by the camera, and detects interaction to select one of the available facial images as a selected patient facial image for maintaining in the data store.

12. The system of claim 11 wherein the user interface further includes at least one interactive control for recapturing at least one new patient facial image.

13. The system of claim 11 wherein the user interface shows medical data of the patient in association with the patient facial image.

14. The system of claim 8 further comprising a user interface that shows the patient facial image in association with medical information associated with that patient facial image, and further shows at least one other patient facial image in association with medical information associated with other patient facial images.

15. The system of claim 14 wherein the patient facial image and the at least one other patient facial image are arranged in a column in different rows of a grid, the rows containing the medical information in other columns.

16. The system of claim 8 wherein the printing device comprises means for printing the patient facial image to an item associated with the patient.

17. One or more computer-readable storage devices having computer-executable instructions, which upon execution perform operations comprising:
determining that data associated with a patient does not have an image representative of the patient assigned to the data;
based on determining that data associated with a patient does not have an image of the patient assigned to the data, automatically acquiring a patient image from documents associated with the patient;
obtaining a plurality of camera shots of the patient;
obtaining information for the camera shots that indicates a bounded region indicative of where a face of the patient appears within respective frames of the camera shots;
clipping the bounded region from the camera shots to obtain facial images of the patient;
displaying the facial images in association with medical information of the patient;
detecting interaction to select a facial image from among the displayed facial images as a selected facial image;
maintaining the selected facial image in association with data by which the patient is identifiable; and
printing the selected facial image and locating the selected image onto one or more medical items associated with the patient including a drug bottle or device associated with the patient to help prevent patient misidentification with respect to the medical item or items.

18. The one or more computer-readable storage devices of claim 17 having further computer-executable instructions comprising providing the camera shots to a face detection algorithm, and receiving information from the face detection algorithm by which the images are clipped from the camera shots.

19. The one or more computer-readable storage devices of claim 17 having further computer-executable instructions comprising adding additional medical data of the patient in association with the facial images.

20. The one or more computer-readable storage devices of claim 17 having further computer-executable instructions comprising storing the selected image with previously saved facial images of the patient in association with medical information of the patient, the saved images and the selected image being used as candidate images for identifying the patient.

* * * * *